(12) United States Patent
Kojima et al.

(10) Patent No.: US 8,091,441 B2
(45) Date of Patent: Jan. 10, 2012

(54) METHOD FOR EVALUATING DISPERSIBILITY OF POWDER AND METHOD FOR EVALUATING CONCENTRATION OF AIRBORNE POWDER, AND METHOD FOR DESIGNING CONTAINMENT FACILITY USING THE SAME

(75) Inventors: Shuzo Kojima, Mito (JP); Shinichi Yamagami, Yokohama (JP); Naruaki Watanabe, Yamato (JP)

(73) Assignee: JGC Corporation, Tokyo (JP)

( * ) Notice: Subject to any disclaimer, the term of this patent is extended or adjusted under 35 U.S.C. 154(b) by 842 days.

(21) Appl. No.: 12/128,937

(22) Filed: May 29, 2008

(65) Prior Publication Data

US 2008/0295620 A1    Dec. 4, 2008

(30) Foreign Application Priority Data

May 30, 2007  (JP) ................................. 2007-143171
Aug. 14, 2007  (JP) ................................. 2007-211386

(51) Int. Cl.
*G01N 33/00* (2006.01)
(52) U.S. Cl. ........................................................ 73/866
(58) Field of Classification Search .................. None
See application file for complete search history.

(56) References Cited

U.S. PATENT DOCUMENTS

| | | | | | |
|---|---|---|---|---|---|
| 3,653,253 | A | * | 4/1972 | Olin | 73/24.03 |
| 3,715,911 | A | * | 2/1973 | Chuan | 73/24.03 |
| 4,107,382 | A | * | 8/1978 | Augustine et al. | 428/368 |
| 4,223,559 | A | * | 9/1980 | Chuan et al. | 73/865.5 |
| 2002/0124632 | A1 | * | 9/2002 | Reiter et al. | 73/24.03 |
| 2006/0021454 | A1 | * | 2/2006 | Rasmussen et al. | 73/865 |

OTHER PUBLICATIONS

Cowherd, C. et al. "An Apparatus and Methodology for Predicting the Dustiness of Materials." American Industrial Hygiene Association Journal. vol. 50, No. 3, p. 123-130 (1989).
Heitbrink, William A. "Factors Affecting the Heubach and MRI Dustiness Tests." American Industrial Hygiene Association Journal. vol. 51, No. 4, p. 210-216 (1990).
Heitbrink, W. A. et al. "Dustiness T esters as a Means of Evaluating the Dust Exposure Potential of Powders." Proceedings of the Technical Program. Annual Powder & Bulk Solids Conference/Exhibition, p. 539-549 (1989).
Carlson, K. H. et al. "A Comparison of Two Dustiness Evaluation Methods." American Industrial Hygiene Association Journal. vol. 53, No. 7, p. 448-454 (1992).
Hamelmann, F. et al. "Methods for Characterizing the Dustiness Estimation of Powders." Chemical, Engineering & Technology. vol. 27, No. 8, p. 884-847 (2004).
Castor, W. et al. "Evaluating the Dustiness of Powders." Powder Handling and Processing. vol. 2, No. 2, p. 145-148 (1990).

\* cited by examiner

*Primary Examiner* — Robert Raevis
(74) *Attorney, Agent, or Firm* — Leason Ellis LLP.

(57) ABSTRACT

A method for evaluating the powder dispersibility including dispersing a powder allowed to stand inside a closed container by mechanical vibration applied quantitatively to the powder; collecting the dispersed powder on a quartz crystal element or a piezo element; and measuring the mass of the collected powder using a quartz crystal microbalance or a piezo element mass meter to thereby measure the airborne powder concentration in air inside the closed container; a method for evaluating airborne powder concentration at work place using the method for evaluating the powder dispersibility; and a method for designing a powder containment facility using the method for evaluating airborne powder concentration.

7 Claims, 7 Drawing Sheets

FIG. 5

METHOD FOR EVALUATING DISPERSIBILITY OF POWDER AND METHOD FOR EVALUATING CONCENTRATION OF AIRBORNE POWDER, AND METHOD FOR DESIGNING CONTAINMENT FACILITY USING THE SAME

BACKGROUND OF THE INVENTION

1. Field of the Invention

The present invention relates to a method for evaluating dispersibility of powder and a method for evaluating concentration of airborne powder especially potent materials, and a method for designing a containment facility for powder using the above methods. More specifically, the present invention relates to a method for evaluating the dispersibility of a powder and a method for evaluating the concentration of airborne powder, in which the dispersibility of the powder is quantitatively evaluated using a trace amount of powder enabling the quantitative design and performance evaluation of a containment facility, and a method for designing a containment facility for the powder using the above methods.

Priority is claimed on Japanese Patent Application No. 2007-143171, filed May 30, 2007, and on Japanese Patent Application No. 2007-211386, filed Aug. 14, 2007, the contents of which are incorporated herein by reference.

2. Description of the Related Art

Conventionally, in the apparatus for measuring powder dispersibility, a method, in which an airborne powder generated in a certain manner is collected on a filter and then chemically quantified, or a method, in which information on the amount of airborne powder is obtained from the laser diffraction data with respect to sample air, has been adopted.

Examples of the apparatus for measuring powder dispersibility which adopts a method to chemically quantify the amount of collected powder include the MI Dustiness Tester developed by Cowherd et al.

In this measuring apparatus, about 100 g of a powder put in a beaker inside a container is dropped to the bottom of the container to disperse the powder (for example, see Cowherd, C. JR, M. A. Grelinger, P. J. Englehart, R. F. Kent, K. F. Wong, "An Apparatus and Methodology for Predicting the Dustiness of Materials", American Industrial Hygiene Association Journal, 50 (3), 1989, pp. 123-130, and Heitbrink W. A., "Factors Affecting the Heubach and MRI Dustiness Tests", American Industrial Hygiene Association Journal, 51 (4), 1990, pp. 210-216.).

Further, in the study by Heubach, 10 to 200 g of a powder put in a rotary drum is dispersed by rotating the rotary drum (for example, see Heitbrink W. A., "Factors Affecting the Heubach and MRI Dustiness Tests", American Industrial Hygiene Association Journal, 51 (4), 1990, pp. 210-216, and Heitbrink W. A., T. C. Cooper, W. F. Todd, D. M. O'Brien, "Dustiness Testers as a means of evaluating the dust exposure potential of powders", Proceedings of the Technical Program. Annual Powder & Bulk Solids Conference/Exhibition, 1989, pp. 539-549).

Furthermore, in the study by Carlson, a powder is dropped from a hopper called "Laboratory Dust Disperser" and the dropped powder is then introduced into a container for measurement using an air blow device that is set perpendicular to the hopper (for example, refer to Carlson K. H., D. R. Herman, T. F. Markey, R. K. Wolff, M. A. Dorato, "A Comparison of Two Dustiness Evaluation Methods", American Industrial Hygiene Association Journal, 53 (7), 1992, pp. 448-454).

With the above methods, although the amount of airborne powder can be evaluated in terms of mass concentration, at least a few tens of milligrams of the powder need to be collected in order to directly measure the powder mass. Therefore, with these methods, a large amount of powder sample is required, making it difficult to measure a toxic powder or an expensive powder.

When a chemical analysis is conducted, measurement will be possible if about a few hundred nanograms of a powder can be collected. Hence, it is possible to reduce the amount of powder sample to about 10 g. However, since the chemical determination is required, it is necessary to select different analytical methods (including pretreatment methods and measuring instruments) for each target powder depending on its chemical composition.

For example, when lactose is quantitatively determined, the entire substance collected on a filter is dissolved in about 10 cc of water since this substance is water soluble, and thus it will be possible to determine the substance down to a level of a few hundred nanograms by analyzing this solution down to a level of 10 ppb using high performance liquid chromatography. However, when dealing with water-insoluble powders, the selection of appropriate solvents is also required. In addition, powders need to be collected for a few hours or even longer in order to secure the required amount of samples.

As described so far, sophisticated knowledge of analytical chemistry is required for the powder analysis, and thus easy measurement of the amount of airborne powder has been a challenge. Especially when the sample is a newly developed API (active pharmaceutical ingredients), measurement of the amount of airborne sample will be extremely difficult due to its low availability and high cost, and also for the lack of established analytical methods.

On the other hand, examples of the devices employing laser diffraction for measuring powder concentration include devices known as the Dust View and the STRIKER.

In the Dust View, 30 g of a powder is dropped all at once in a container to disperse the powder (for example, see Hamelmann F., E. Schmidt, "Methods for Characterizing the Dustiness Estimation of Powders", Chemical Engineering & Technology, 27 (8), 2004, pp. 844-847.).

In the STRIKER, a container known as a cuvette containing powder is patted several times at its bottom by a beating device equipped with a spring to disperse the powder (for example, see Castor W., A. Gray, "Evaluating the dustiness of powders", Powder Handling & Processing, 2 (2), 1990, pp. 145-148.).

With these methods, information on the number concentration can be obtained rapidly as the powder measurement is performed using a laser. However, information on particle size and density is required for converting the number information to the mass data. Moreover, although the conversion is readily made if the shape of the particles is simply spherical, the actual powder has a complex shape, and thus the conversion has not been easy. Furthermore, since different types of powders have different shapes, comparison between different powders has been even harder.

SUMMARY OF THE INVENTION

The following problems have been associated with the above-mentioned conventional methods for evaluating powder dispersibility (e.g. dustiness index).

A large amount of powder is needed in the method to obtain mass concentration necessary for exposure assessment. Accordingly, it has been difficult to evaluate the dispersibility of expensive APIs or highly potent APIs due to economic or safety reasons. In addition, the conventional methods require chemical analysis, and thus long time period are needed for evaluating a variety of APIs.

On the other hand, in the evaluation methods using a small amount of samples, conversion of the information on powder to the mass data, that are required for worker exposure assessment, has been difficult. This is because it is necessary to evaluate the mass of the API to be inhaled by a worker for the exposure assessment, and thus the powder dispersibility needs to be summarized in the form of mass concentration rather than the number concentration in air or laser scattering properties.

Moreover, comparison of the amount of airborne powder between different APIs has been difficult with the conventional methods. Hence, when dealing with various powders (APIs), it has been difficult to measure the amount of airborne powder without employing any special analytical methods including chemical analysis.

Although various methods for dispersing powders have been proposed such as the dropping method, the rotating method, the air blowing method, and the beating method described above, it has been difficult in principle to achieve a high level repeatability with any of these methods.

Prediction of the amount of powder inhalation (I) by a worker in the powder handling process can be made by the following formula (1).

$$I=C\times B\times T\times P \quad (1)$$

In the above formula (1), I represents the amount of powder inhalation [μg], C represents the powder concentration in the working environment [$\mu g/m^3$], B represents the respiration rate [$m^3/h$], T represents the operation time [h], and P represents the protection factor of a protection equipment.

In addition, powder concentration in the working environment can be predicted by the following formula (2).

$$C=k\times(1/V)\times E\times A\times M\times F \quad (2)$$

In the above formula (2), C represents the powder concentration in the working environment [$\mu g/m^3$], k represents a proportionality coefficient, V represents the ventilation rate in the working environment [1/h], E represents the containment performance of an equipment, A represents the work-dependent dispersion strength, M represents the amount of powder processed per unit time [kg/h], and F represents the powder dispersibility [$((\mu g/m^3)\cdot(1/h))/(kg/h)$].

However, at present, the powder dispersibility F remains to represent mere qualitative values, for example, 10, 1, and 0.1 for dry powder, wet powder, and solidifying agent, respectively. As a result, quantitative dispersibility of dry powder could not be discussed. Moreover, no quantitative evaluation has been made to date on the parameters such as the work-dependent dispersion strength A and the equipment's containment performance E.

Furthermore, in the trial operation when handling the actual powder, airborne powder concentration was difficult to predict from the data on containment-performance evaluation test using standard powders such as lactose.

From the above reasons, it has been impossible to predict the airborne powder concentration from a dustiness index obtained by the conventional methods.

The present invention has been made in view of the above circumstances with an object of providing a method for evaluating powder dispersibility and a method for evaluating airborne powder concentration which are capable of evaluating powder dispersibility using a small amount of samples, capable of evaluating mass concentration required in the exposure control, capable of mass measurement of various powder materials without employing any special analytical methods such as chemical analysis, and capable of predicting the airborne powder concentration of actual target powder from the obtained “airborne index” (new concept dustiness index). Another object of the present invention is to provide a method for designing a powder containment facility using the above methods.

The present invention provides a method for evaluating powder dispersibility in which the concentration of airborne powder allowed to stand inside a closed container is measured by dispersing the powder material inside the closed container by the mechanical vibration applied quantitatively to the powder, collecting this dispersed powder on a quartz crystal element or a piezo element, and measuring the mass of this collected powder using a quartz crystal microbalance or a piezo element mass meter to thereby measure the airborne powder concentration in the air inside the closed container.

In the present invention, it is preferable that the mass of the powder allowed to stand inside the closed container be within a range from 0.1 g to 5 g.

The present invention also provides a method for evaluating airborne powder concentration by measuring airborne powder concentration of a surrogate powder by the method for evaluating powder dispersibility of the present invention; calculating the logarithm of the airborne powder concentration (airborne index d); measuring the airborne concentration C' of the surrogate powder in a working environment; producing a calibration curve F(d) from the airborne index d and the airborne concentration C'; and predicting the airborne concentration C of an actual target powder in the working environment from the airborne index d of the actual target powder using the calibration curve F(d).

The present invention also provides a method for designing a powder containment facility by predicting dispersibility of an actual target powder in an actual working environment by the method for evaluating airborne powder concentration of the present invention; and designing a powder containment facility based on the predicted results.

By the method for evaluating powder dispersibility according to the present invention, powder dispersibility can be evaluated using a small amount of samples, thereby enabling the dispersibility evaluation of the powders such as an expensive API at low cost Moreover, since the powder dispersibility can be evaluated with a small amount of samples, when an evaluation is made using a highly active powder, the risk of exposing an individual to such a potentially hazardous powder can be reduced. In addition, since mass of the powder contained in the working environment atmosphere can be measured instantly, time for measuring the yardstick of powder dispersibility (airborne index) can be extremely shortened. Moreover, powder dispersibility can be evaluated based on the information on powder mass, which is required for the worker exposure assessment. Furthermore, particle size distribution of the airborne powder can also be determined by using a cascade impactor.

By the method for evaluating airborne powder concentration according to the present invention, evaluation on the containment performance with respect to the actual target powder in the actual powder-handling process can be made using a standard powder (surrogate powder).

BRIEF DESCRIPTION OF THE DRAWINGS

FIG. 1 is a schematic configuration diagram showing an apparatus for evaluating powder dispersibility used in a method for evaluating powder dispersibility according to the present invention.

FIG. 2 is a graph showing a relationship between the mass of test powder and the airborne powder concentration in the flask in Example 1 of the present invention.

FIG. 5 is a graph showing a relationship between the airborne index, which is obtained by the method for evaluating the powder dispersibility according to the present invention, and airborne powder concentration in the actual operation in Example 4 of the present invention.

DESCRIPTION OF THE REFERENCE NUMERALS

10: Apparatus for evaluating powder dispersibility; 11: First filter; 12: Closed container; 13: Cascade impactor; 14: Second filter; 15: Air pump; 16: Vibratory device.

DETAILED DESCRIPTION OF THE INVENTION

Preferred embodiments of the method for evaluating powder dispersibility and the method for evaluating airborne powder concentration according to the present invention will be described.

Note that these embodiments are provided to specifically describe the present invention for better understanding of the scope thereof, and are not for limiting the present invention unless specifically stated otherwise.

[Method for Evaluating Powder Dispersibility]

Figure 1:
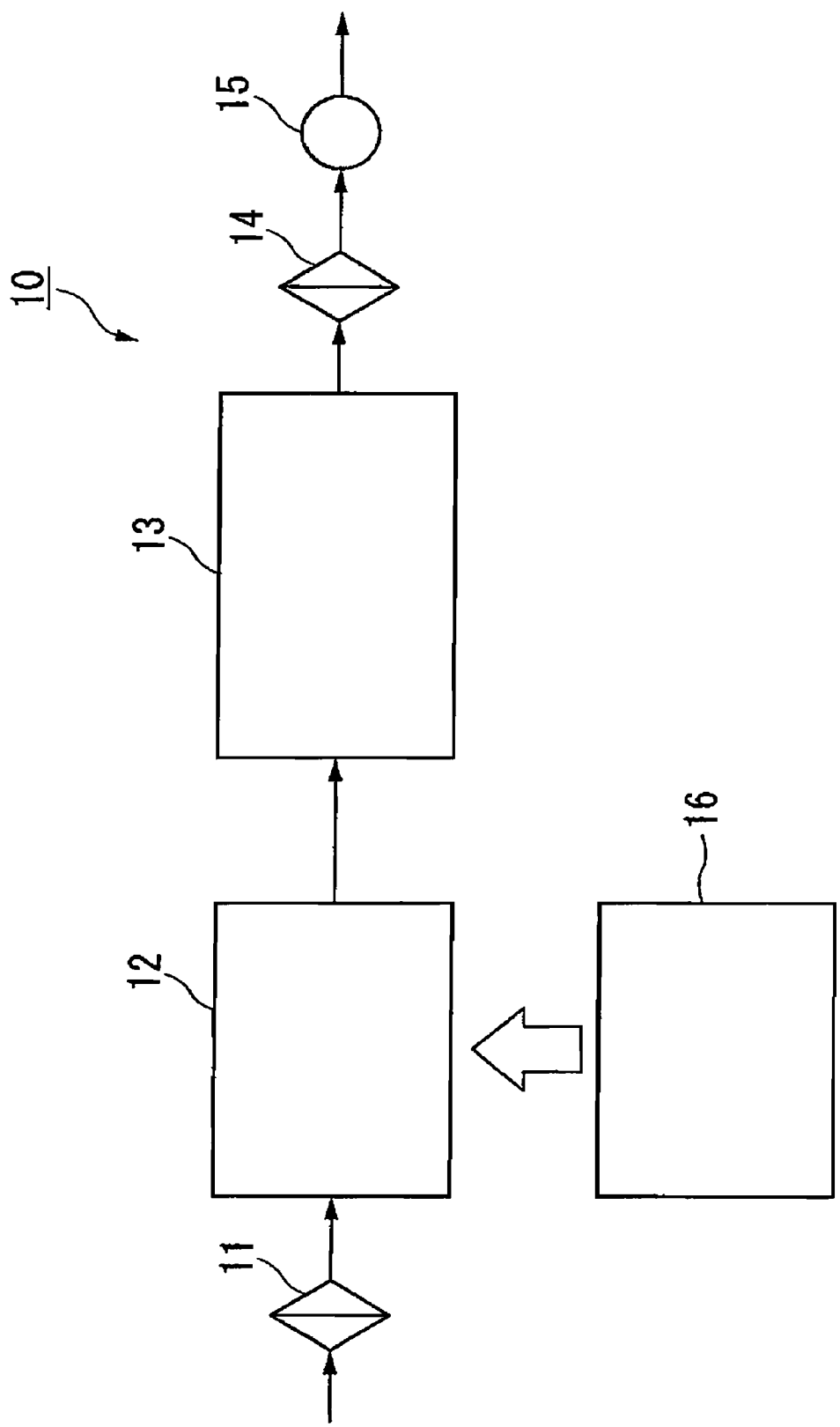

FIG. 1 is a schematic configuration diagram showing an apparatus for evaluating powder dispersibility used in a method for evaluating powder dispersibility of the present invention.

This apparatus 10 for evaluating powder dispersibility is generally constituted of a first filter 11, a closed container 12, a cascade impactor 13, a second filter 14, and an air pump 15, which are connected in this order through a conduit, and a vibratory device 16, which applies vibration to the closed container 12.

As the first filter 11, an air filter made of a typical non-woven fabric or the like can be used. This first filter 11 is provided in order to remove the contaminant particles (particles other than the powders, which are the measurement target such as a API) in the air that are introduced into the closed container 12 so as to improve measurement accuracy.

The cascade impactor 13 is a device for collecting airborne powder onto quarts crystal elements due to the inertial impaction between the particles. The cascade impactor 13 is configured so that numerous sizing stages which collect these particles are connected in series in the vertical direction, and that the particles are collected depending on their size beginning with the largest particles collected at the uppermost sizing stage.

A quartz crystal element is provided inside each sizing stage of the cascade impactor 13 so that the particles having a particle size within a predetermined range are collected on this quartz crystal element.

Moreover, a quartz crystal microbalance is provided inside each sizing stage of the cascade impactor 13 so as to weigh the particles collected by the quartz crystal element provided in the same sizing stage.

As the cascade impactor 13 described above, for example, the QCM cascade impactor (Model PC-2 manufactured by California Measurements, Inc) can be used. As a method for collecting powdered particles other than those using a cascade impactor, electrostatic collection methods such as a collection method employing a piezo balance dust meter (Model 3521 manufactured by Kanomax Japan Inc.) can be used.

This cascade impactor 13 is capable of measuring particle size distribution based on the mass of trace particles collected on the quartz crystal element within a short period of a few tens of seconds, and also capable of instantly measuring the amount of particles in the air separately based on the particle size.

The closed container 12 is not particularly limited and any container may be used as long as the container can enclose a certain amount of powder and the enclosed powder can be dispersed inside when vibrated by the vibratory device 16.

As the second filter 14, an air filter made of a typical non-woven fabric or the like can be used. This second filter 14 is provided in order to remove the particles contained in the air to be sucked by the air pump 15 so as to prevent the air pump 15 from failing by suctioning the particles.

The air pump 15 is used for introducing the air inside the closed container 12 that contains particles into the cascade impactor 13 at a constant flow rate.

The vibratory device 16 is not particularly limited as long as the device can apply mechanical vibration quantitatively to the closed container 12 and, for example, a vibration generator or a Vortex (trade name) can be used.

The term "quantitatively" used herein refers to the state where intensity of the mechanical vibration applied to the closed container 12 can be described in numerical values and also the application of mechanical vibration at a certain intensity is reproducible.

Next, the method for evaluating powder dispersibility according to the present invention will be described.

The method for evaluating powder dispersibility according to the present invention is a method in which the concentration of airborne powder inside the closed container 12 is measured by dispersing the powder allowed to stand inside the closed container 12 by the mechanical vibration applied quantitatively by the vibratory device 16 to the powder, collecting this dispersed powder on a quartz crystal element provided inside the cascade impactor 13, and measuring the mass of this collected powder using a quartz crystal microbalance provided inside the cascade impactor 13.

The powder that can be evaluated by the method for evaluating powder dispersibility of the present invention is not particularly limited and the dispersibility evaluation can be performed with respect to any powders.

The method for evaluating powder dispersibility according to the present invention will be described in detail below.

Firstly, a predetermined amount of powder is enclosed in the closed container 12, and using the air from which contaminant particles are substantially removed by the first filter 11, the air inside the closed container 12 is replaced with clean air.

Mass of the powder enclosed in the closed container 12 is preferably within the range from 0.1 g to 5 g and more preferably from 0.1 g to 3 g.

Mass of the powder enclosed in the closed container 12 is preferably within the range from 0.1 g to 5 g because when the powder mass is less than 0.1 g, the amount of powder is too small for the powder concentration measurement by the cascade impactor 13, whereas the powder mass of more than 5 g will result in large measurement errors (variations) in the powder concentration measurement by the cascade impactor 13.

In addition, the volume of the closed container 12, that is the volume of space in which powder is dispersed, is preferably within the range from 100 ml to 300 ml.

Volume of the closed container 12 is preferably within the range from 100 ml to 300 ml for the following reasons. When the volume is less than 100 ml, measurements cannot be made with high reproducibility in the powder concentration measurement by the cascade impactor 13 due to problems such as the portion of powder being attached to the wall surface of the closed container 12. On the other hand, when the volume of the closed container 12 exceeds 300 ml, it becomes impossible to disperse a small amount of powder in the air inside the closed container 12 at a high concentration, and thus the concentration measurements of trace powder cannot be made.

Then the powder is dispersed (suspended) inside the closed container 12 by applying mechanical vibration quantitatively to the closed container 12 by the vibratory device 16.

The period for applying mechanical vibration quantitatively to the closed container 12 by the vibratory device 16 is preferably within a range from 10 seconds to 15 seconds.

The period for applying mechanical vibration quantitatively to the closed container 12 by the vibratory device 16 is preferably within a range from 10 seconds to 15 seconds for the following reasons. When the application period is less than 10 seconds, the airborne powder concentration (that is, concentration of powder dispersed in air which will hereinafter simply be referred to as "airborne concentration") will be too low for the powder concentration measurement by the cascade impactor 13. On the other hand, the application time of more than 15 seconds will result in large measurement errors (variations) in the powder concentration measurement by the cascade impactor 13.

Then the powder dispersed in the air inside the closed container 12 is collected on the quartz crystal element provided in the cascade impactor 13 by suctioning (collecting) the air inside the closed container 12 that contains the powder (the air in which the powder is dispersed) into the cascade impactor 13.

The time for collecting the powder dispersed in the air inside the closed container 12 by the cascade impactor 13 (sampling time) is preferably within a range from 150 seconds to 200 seconds.

A sampling period of 150 seconds to 200 seconds is preferable for the following reasons. When the sampling period is less than 150 seconds, although a high airborne concentration is achieved, variations in the airborne concentration become large. On the other hand, when the sampling time is more than 200 seconds, the airborne concentration becomes low.

Subsequently, mass of the powder collected on the quartz crystal element is measured using a quartz crystal microbalance or a piezo element mass meter provided inside the cascade impactor 13.

Thereafter, airborne powder concentration in the closed container 12 is calculated from the obtained powder mass and the amount of air collected in the cascade impactor 13.

By the method for evaluating the powder dispersibility according to the present invention, the powder dispersibility can be evaluated using a small amount of samples, thereby enabling the dispersibility evaluation of the powders such as an expensive API at low cost. Moreover, since the powder dispersibility can be evaluated with a small amount of samples, when an evaluation is made using a highly active powder, the risk of exposing an individual to such a potentially hazardous powder can be reduced. In addition, since the powder concentration can be measured instantly, time for measuring the yardstick of the powder dispersibility (airborne index) can be extremely shortened. Moreover, the powder dispersibility can be evaluated based on the information on powder mass, which is required for the powder exposure control. Furthermore, particle size distribution of the airborne powder can also be determined by using a cascade impactor.

[Method for Evaluating Airborne Powder Concentration]

In the method for evaluating the airborne powder concentration according to the present invention, the logarithm of the airborne concentration of a surrogate powder (airborne index d) measured using the method for evaluating powder dispersibility according to the present invention is first calculated. Separately from the above, the airborne concentration C' of the surrogate powder in the working environment is measured. Then a calibration curve F(d) is derived from the airborne index d and the airborne concentration C', and finally the airborne concentration C of the actual target powder in the working environment is predicted from the airborne index d using the calibration curve F(d).

Specifically, the airborne index d with respect to the surrogate powder is derived by calculating the logarithm of the airborne concentration measured using the method for evaluating powder dispersibility according to the present invention.

Separately from this, the airborne concentration C' with respect to a surrogate powder in the actual working environment is measured.

Then a graph is plotted in which the horizontal axis represents the airborne index d and the vertical axis represents the logarithm of the airborne powder concentration C' in the actual working environment.

A calibration curve F(d) is derived from the linear regression of the plotted points employing the least squares method.

Using this calibration curve F(d), the airborne powder concentration C of the actual target powder in the targeted working environment is predicted from the airborne index d of the actual target powder.

In other words, once the calibration curve F(d) is obtained, it will be possible to predict the airborne powder concentration C of the actual target powder in an industrial scale working environment by measuring the airborne powder concentration of the actual target powder in the closed container and calculating the airborne index d from this airborne powder concentration.

The airborne powder concentration C in the working environment which is predicted as described above can be expressed by the following formula (3).

$$C=k'\times G(h,t)\times(1/V)\times E\times A\times M\times F(d) \quad (3)$$

In the formula (3), C represents the powder concentration in the working environment [μg/m$^3$], k' represents a proportionality coefficient, G(h, t) represents a constant that is dependent on humidity h and on temperature t, V represents the ventilation rate in the working environment [1/h], E represents the containment performance of an equipment, A represents the work-dependent dispersion strength, M represents the amount of powder handled per unit time [kg/h], and F(d) represents the powder dispersibility [((μg/m$^3$)·(1/h))/(kg/h)] which is the airborne powder concentration when the powder having an airborne index d is processed at 1 kg/h by the standard operation in an environment with a unit ventilation rate of 1/h.

The work-dependent dispersion strength A is, for example, 1 for the transfer operation of a certain procedure, 10 for the sieving operation of a certain procedure, and 0.5 for the dispensing operation of a certain procedure, when the above operations are defined as the standard operation.

The equipment's containment performance E is, for example, 1 when no equipment is available, 0.01 when a certain safety hood is available, and 0.001 when a certain down flow booth is available.

By the method for evaluating airborne powder concentration according to the present invention, evaluation on the powder containment performance in the actual powder-handling process can be made using a standard powder.

Examples where the evaluation on powder containment performance is required include the containment facilities found in the pharmaceutical and API manufacturing plants which handle APIs and chemical plants which handle highly active powders such as agricultural chemicals. Such containment facilities have a function to reduce the risk of exposing a worker to the chemicals, which are handled mainly in powder form, and a function to prevent the leakage of powder to the environment surrounding the facilities. By incorporating the method for evaluating the airborne powder concentration according to the present invention to a process of designing such containment facilities, it becomes possible to design a facility, which takes easy powder dispersion into account.

EXAMPLES

The present invention will be described below in further details using Examples. However, the present invention is not limited to these Examples.

Example 1

Effects of a powder's mass on the airborne powder concentration was examined using an apparatus for evaluating powder dispersibility as shown in FIG. 1.

Various conditions adopted in this Example 1 were as follows.

A flask having a volume of 300 ml was used as a closed container.

The airborne powder in the closed container was collected and measured by a cascade impactor.

Lactose (manufactured by DMV Farm) was used as a powder.

The mass of lactose was changed to 0.1 g, 0.2 g, 0.5 g, 1 g, 2 g, 3 g, 5 g, and 10 g, to measure the airborne lactose concentration in the closed container.

The measurements were made once to three times for the respective lactose masses.

Figure 2:
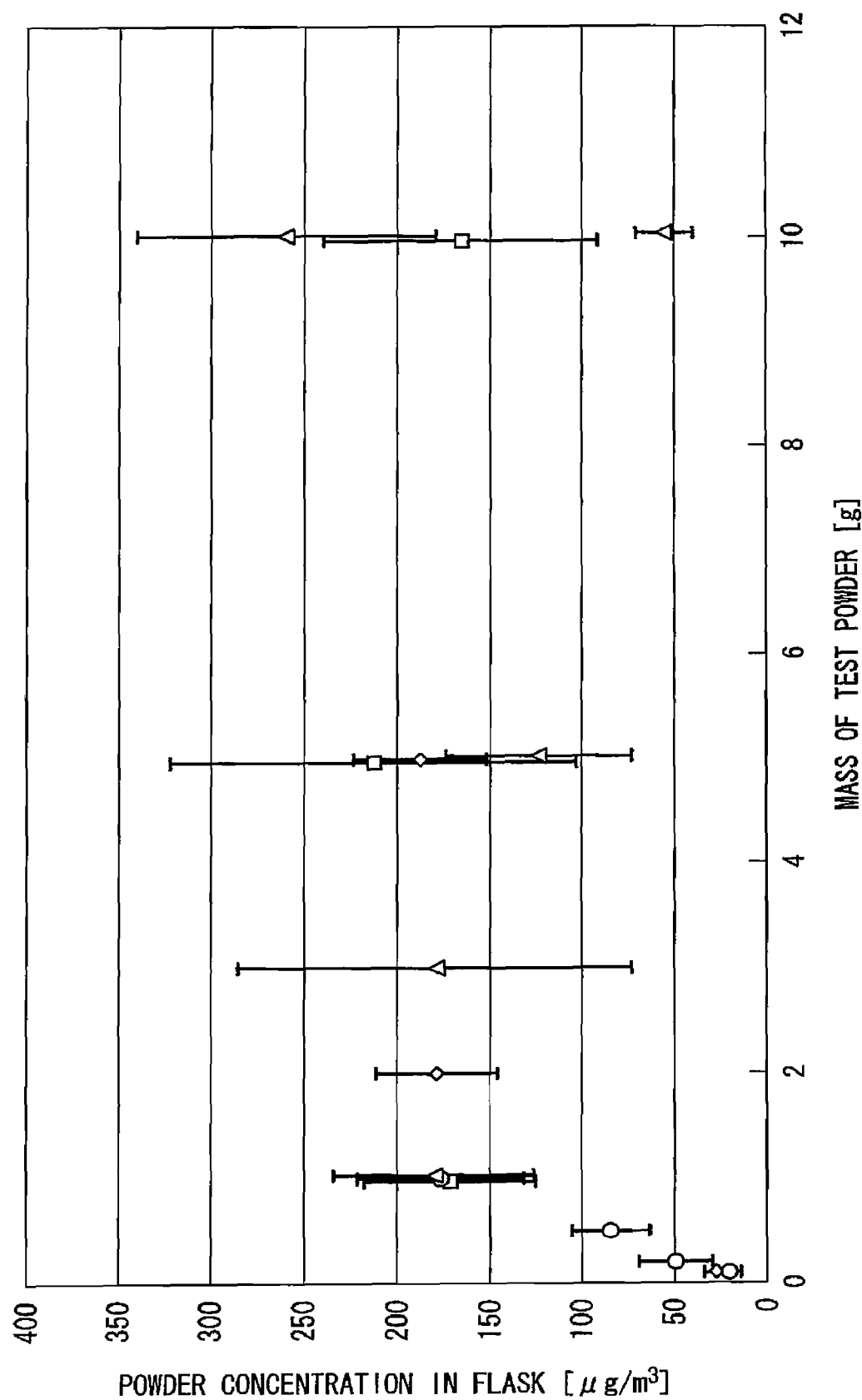

Results are shown in FIG. 2.

From the results shown in FIG. 2, it was found that when the powder (lactose) mass in the flask was 1 g or more, the powder concentration in the flask became almost constant, in other words, the amount of powder put inside the flask no longer affected the measured value greatly resulting in a suitable condition for the apparatus to measure airborne index. However, when the powder mass exceeded 5 g, it was confirmed that variations in the measured value became large. Note that the powder mass needed to be measured accurately (weighed accurately) even though measurements could be made with a powder mass of only 0.1 g.

Example 2

1.0 g of each of the following powders was prepared: i.e., calcium chloride (manufactured by Wako Pure Chemical Industries, Ltd.), potassium chloride (manufactured by Wako Pure Chemical Industries, Ltd.), sodium chloride (manufactured by Wako Pure Chemical Industries, Ltd.), sodium sulfate (manufactured by Wako Pure Chemical Industries, Ltd.), sodium bicarbonate (manufactured by Wako Pure Chemical Industries, Ltd.), magnesium stearate (manufactured by Wako Pure Chemical Industries, Ltd.), magnesium oxide (manufactured by Wako Pure Chemical Industries, Ltd.), acetaminophen PP (manufactured by Hachidai Pharmaceutical Co., Ltd.), acetaminophen P (manufactured by Hachidai Pharmaceutical Co., Ltd.), glucose (manufactured by Wako Pure Chemical Industries, Ltd.), lactose 450M (manufactured by DMV International BV), mannitol (manufactured by Wako Pure Chemical Industries, Ltd.), sorbitol (manufactured by Wako Pure Chemical Industries, Ltd.), lactose 100M (manufactured by DMV International BV), lactose 200M (manufactured by DMV International BV), carpine F 2000 (manufactured by Hachidai Pharmaceutical Co., Ltd.), calsee F 9850 (manufactured by Hachidai Pharmaceutical Co., Ltd.), and calsee F 6402 (manufactured by Hachidai Pharmaceutical Co., Ltd.). By using the apparatus for evaluating powder dispersibility as shown in FIG. 1, the airborne powder concentration of the above powders in the closed container 12 was measured, and the airborne index was derived by calculating the logarithm of the airborne powder concentration (measurement A).

In addition, in an operation to transfer a predetermined amount of powder from the original container to another container at a desk in a down flow booth, the airborne powder concentration C' in the working environment was measured when handling each powder. The airborne particles collected on a cassette filter were dissolved in an appropriate solvent (water, an alcohol, or the like). The amount of powder collected was determined by conducting an appropriate chemical analysis (ion chromatography, ICP-AES, or the like) depending on the targeted powder, and the airborne powder concentration was determined by dividing this amount of powder collected with the amount of air collected (measurement B).

Figure 3:
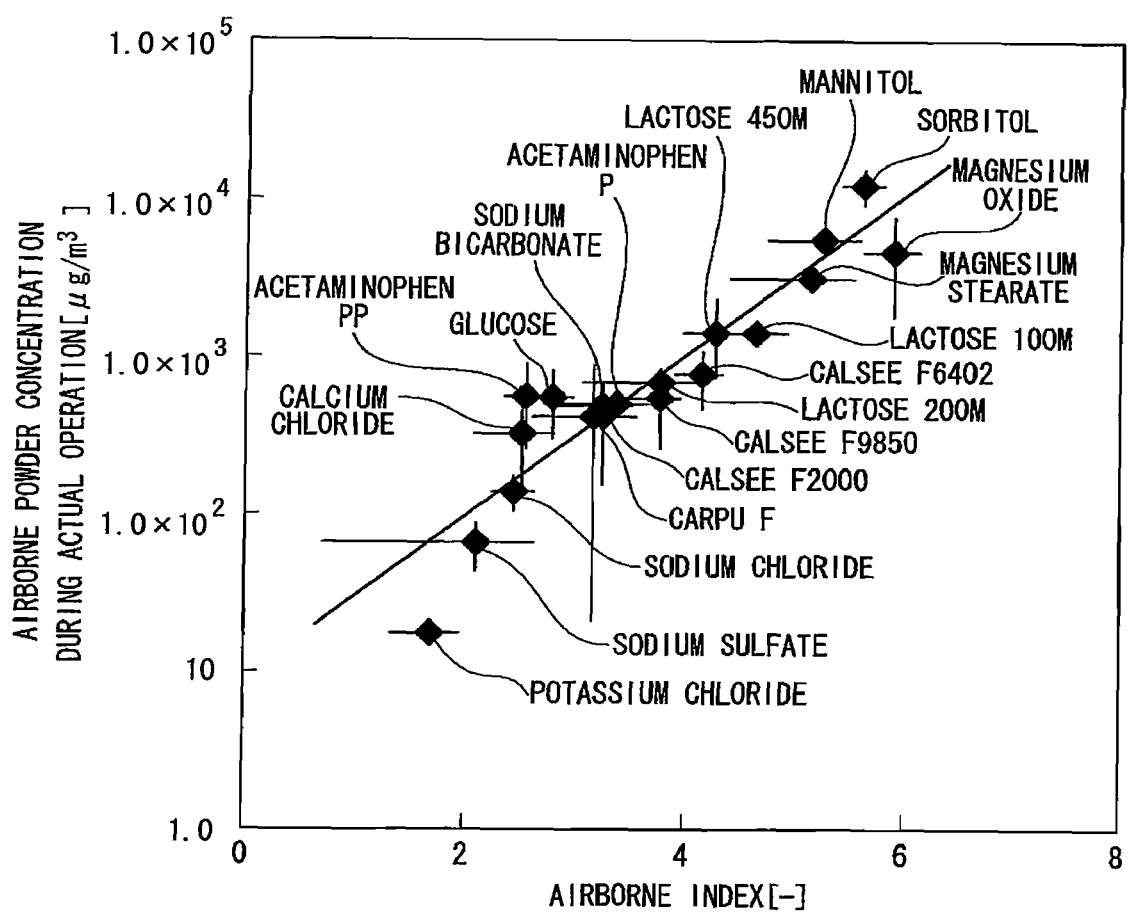
FIG. 3 is a graph showing a relationship between the airborne index, which is obtained by the method for evaluating the powder dispersibility according to the present invention, and the airborne powder concentration during the actual operation in Example 2 of the present invention.

The airborne index obtained in the measurement A was plotted against the airborne powder concentration obtained in the measurement B for the respective powders and an approximation curve was obtained by the linear regression of these plotted points due to the employment of the least squares method. Results are shown in FIG. 3.

From the obtained approximation curve, it was verified that the airborne index obtained in the measurement A was almost proportional to the logarithm of the airborne powder concentration obtained in the measurement B.

From the airborne powder concentration in the working environment obtained in the actual facility during a trial operation using a surrogate powder, it has been impossible to evaluate the airborne powder concentration in the process handling the actual powder. However, from the above results, it was found that it is possible to evaluate the airborne powder concentration when handling the actual target powder by using the airborne indices of the actual target powder and the surrogate powder.

Example 3

The relationship between the airborne index and the airborne powder concentration was examined when a different operation from that in Example 2 was conducted in the same environment to that of Example 2.

1.0 g of each of the following powders was prepared: i.e., sorbitol (manufactured by Wako Pure Chemical Industries, Ltd.), mannitol (manufactured by Wako Pure Chemical Industries, Ltd.), lactose 100M (manufactured by DMV International BV), glucose (manufactured by Wako Pure Chemical Industries, Ltd.), and hydrogen bicarbonate (manufactured by Wako Pure Chemical Industries, Ltd.). By using the apparatus for evaluating powder dispersibility as shown in FIG. 1, airborne powder concentration of the above powders in the closed container 12 was measured, and the airborne index was derived by calculating the logarithm of the airborne powder concentration (measurement C).

In addition, the airborne powder concentration C' in the working environment was measured when handling each powder in an operation to transfer a predetermined amount of powder from the original container to another container at a desk in a down flow booth, and in a sieving operation and a dispensing operation. The airborne particles collected on a cassette filter were dissolved in an appropriate solvent (water, an alcohol, or the like). The amount of powder collected was determined by conducting an appropriate chemical analysis (ion chromatography, ICP-AES, or the like) depending on the target powder, and the airborne powder concentration was determined by dividing this amount of powder collected with the amount of air collected (measurement D).

Figure 4:
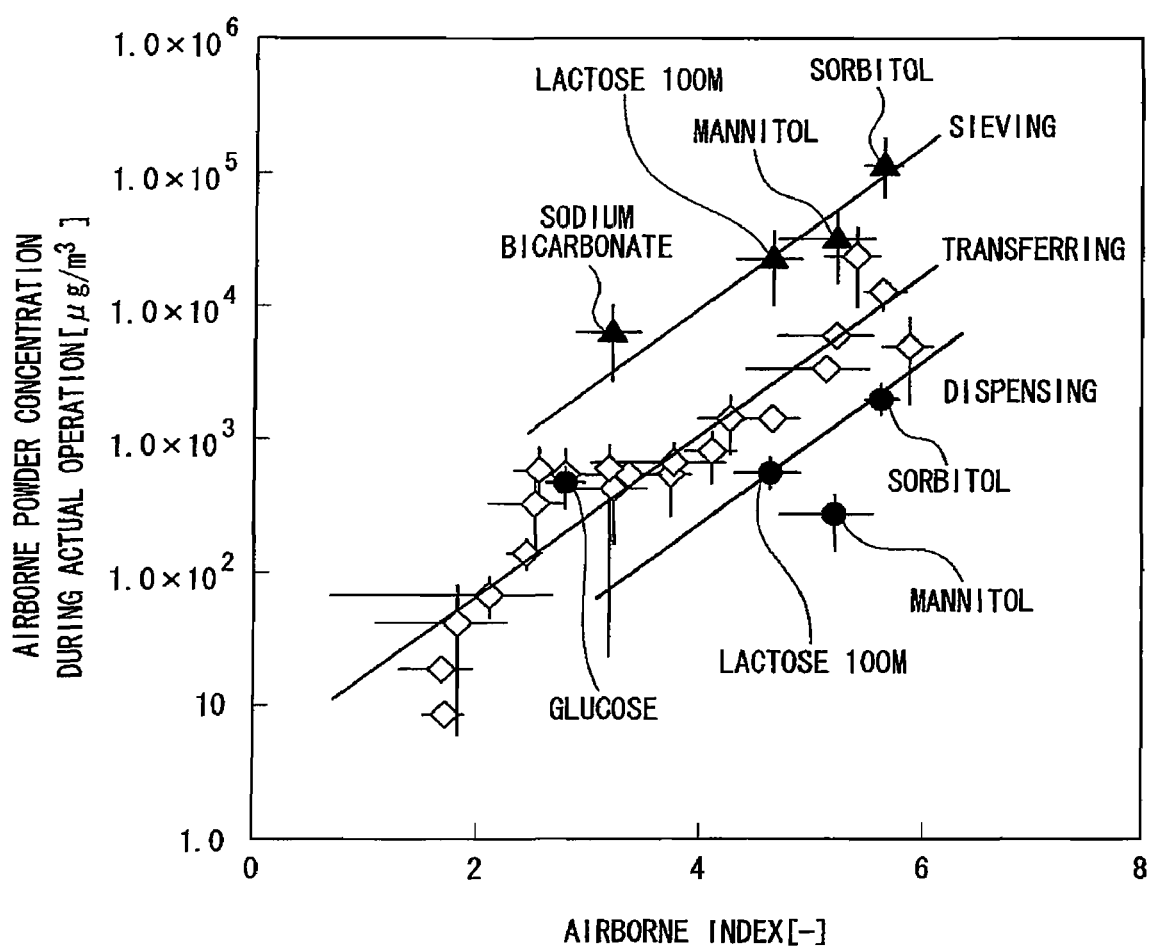
FIG. 4 is a graph showing a relationship between the airborne index, which is obtained by the method for evaluating the powder dispersibility according to the present invention, and airborne powder concentration in the actual operation in Example 3 of the present invention.

The airborne index obtained in the measurement C was plotted against the airborne powder concentration obtained in the measurement D for the respective powders, and an approximation curve was obtained by the linear regression of these plotted points due to the employment of the least squares method. Results are shown in FIG. 4.

From the obtained approximation curve, it was confirmed that the airborne index obtained in the measurement C was almost proportional to the logarithm of the airborne powder concentration obtained in the measurement D even when different operations are conducted.

Moreover, it was confirmed that the sieving operation is an operation generating about times as much airborne powder as that generated in the transfer operation under the conditions of the present examination, and that the dispensing operation is an operation generating about ½ times as much airborne powder as that generated in the transfer operation under the conditions of the present examination.

Example 4

The relationship between the airborne index and the airborne powder concentration was examined when the same operation was conducted in different containment equipment.

1.0 g of each of the following powders was prepared: i.e., sorbitol (manufactured by Wako Pure Chemical Industries, Ltd.), mannitol (manufactured by Wako Pure Chemical Industries, Ltd.), lactose 100 M (manufactured by DMV International BV), and glucose (manufactured by Wako Pure Chemical Industries, Ltd.). By using the apparatus for evaluating powder dispersibility as shown in FIG. 1, the airborne powder concentration of the above powders in the closed container 12 was measured, and the airborne index was derived by calculating the logarithm of the airborne powder concentration (measurement E).

In addition, in an operation to transfer a predetermined amount of powder from the original container to another container in a down flow booth or in a safety hood or with no containment equipment, the airborne powder concentration C' in the working environment was measured when handling each powder. The airborne particles collected on a cassette filter were dissolved in an appropriate solvent (water, an alcohol, or the like). The amount of powder collected was determined by conducting an appropriate chemical analysis (ion chromatography, ICP-AES, or the like) depending on the target powder, and the airborne powder concentration was determined by dividing this amount of powder collected with the amount of air collected (measurement F). It should be noted that the measurement of this airborne powder concentration is measuring the powder concentration in the air, which is equivalent to the worker's exhaled air.

Figure 5:
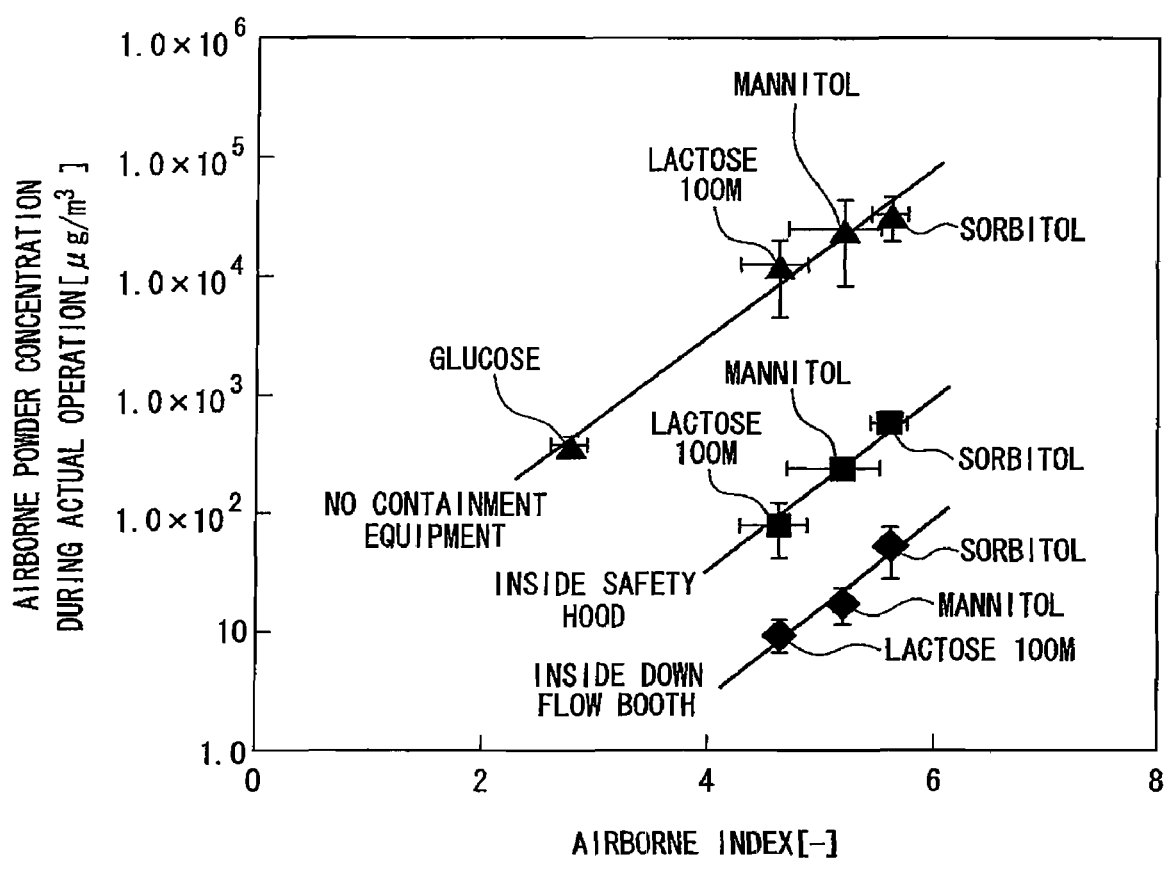

The airborne index obtained in the measurement E was plotted against the airborne powder concentration obtained in the measurement F for the respective powders, and an approximation curve was obtained by the linear regression of these plotted points due to the employment of the least squares method. Results are shown in FIG. 5.

From the obtained approximation curve, it was confirmed that the airborne index obtained in the measurement E was almost proportional to the logarithm of the airborne powder concentration obtained in the measurement F even when different containment equipment was used.

Moreover, it was confirmed that, compared to the case where no containment equipment was available, the airborne powder concentration could be reduced down to about $1/100$ by using a safety hood employed in the present examination, and the airborne powder concentration could be reduced to about $1/1000$ by using a down flow booth employed in the present examination.

Example 5

The approximation curve obtained in Example 2 was adopted as a calibration curve F(d).

By using this calibration curve F(d) as well as the results of measurements A and E obtained in Examples 3 and 4, the target airborne powder concentration in the working environment was predicted from the airborne indices d of the following target powders (lactose (manufactured by Wako Pure Chemical Industries, Ltd.), sorbitol (manufactured by Wako Pure Chemical Industries, Ltd.), glucose (manufactured by Wako Pure Chemical Industries, Ltd.), mannitol (manufactured by Wako Pure Chemical Industries, Ltd.), calcium hydroxide (manufactured by Wako Pure Chemical Industries, Ltd.), sodium ascorbate (manufactured by Wako Pure Chemical Industries, Ltd.), and boric acid (manufactured by Wako Pure Chemical Industries, Ltd.)).

Figure 6:
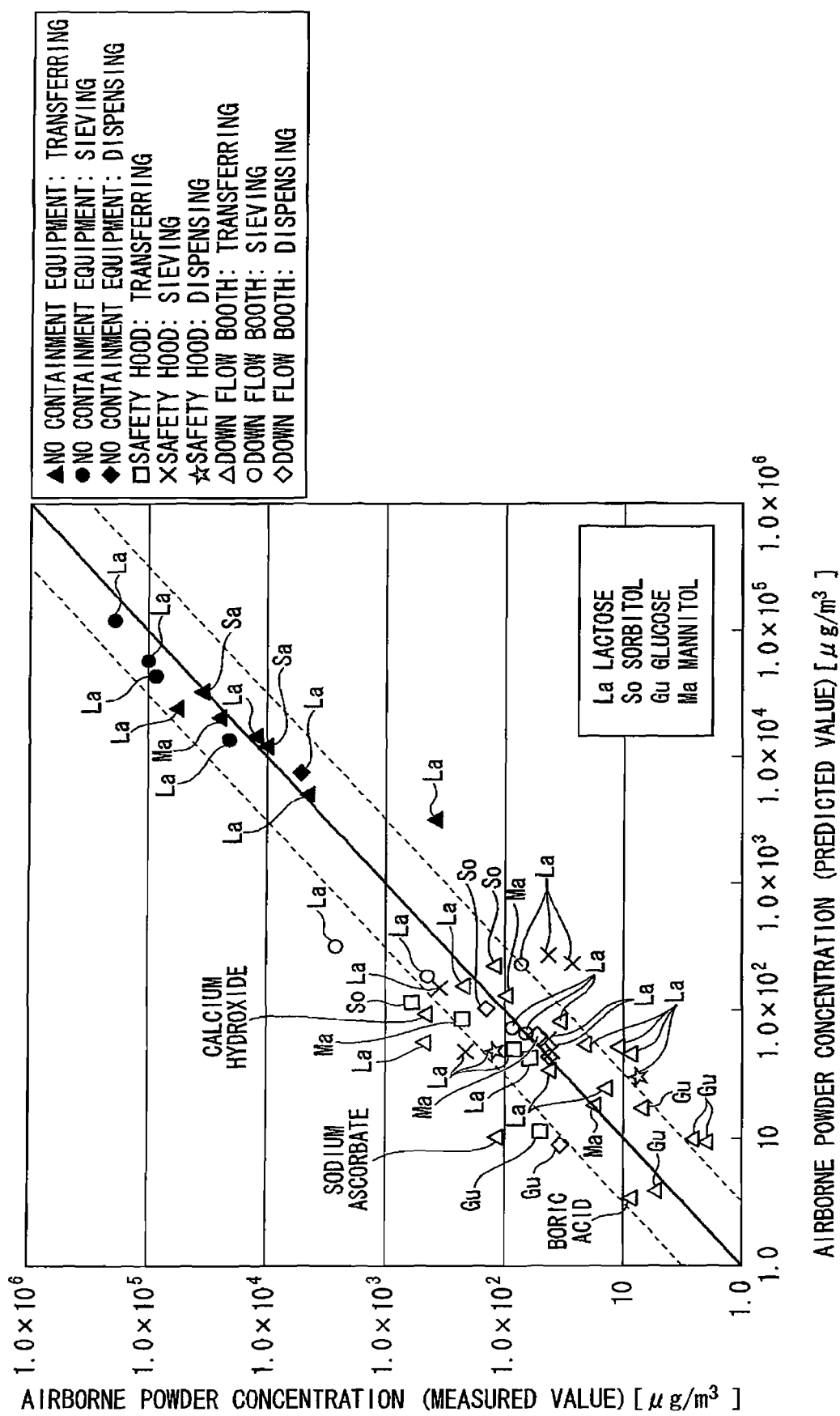
FIG. 6 is a graph showing a relationship between the airborne powder concentration (predicted value), which is obtained by the method for evaluating the airborne powder concentration according to the present invention, and the airborne powder concentration in the actual operation (actual measured value) in Example 5 of the present invention.

The obtained airborne powder concentration (predicted value) was plotted against the airborne powder concentrations (actual measured value) obtained in Examples 3 and 4, and an approximation curve was obtained by the linear regression of these plotted points due to the employment of the least squares method. Results are shown in FIG. 6.

Using the method developed in the present invention, it was confirmed that the airborne powder concentration could be predicted with an accuracy of a factor of about 3.

Example 6

The airborne powder concentration was measured using an apparatus for evaluating powder dispersibility as shown in FIG. 1.

Various conditions adopted in this Example 6 were as follows.

0.1 g of sorbitol (manufactured by Wako Pure Chemical Industries, Ltd.), 0.1 g of lactose 100M (manufactured by DMV International BV), and 0.1 g of glucose (manufactured by Wako Pure Chemical Industries, Ltd.) were used as powders.

A flask having a volume of 300 ml was used as a closed container.

The airborne powder in the closed container was collected and measured by a cascade impactor.

The airborne index was derived by calculating the logarithm of the obtained airborne powder concentration (measurement G).

In addition, in an operation to transfer a predetermined amount of powder from the original container to another container at a desk in a down flow booth, the airborne powder concentration C' in the working environment was measured when handling each powder. The airborne particles collected on a cassette filter were dissolved in an appropriate solvent (water, an alcohol, or the like). The amount of powder collected was determined by conducting an appropriate chemical analysis (ion chromatography, ICP-AES, or the like) depending on the target powder, and the airborne powder concentration was determined by dividing this amount of powder collected with the amount of air collected (measurement H).

Figure 7:
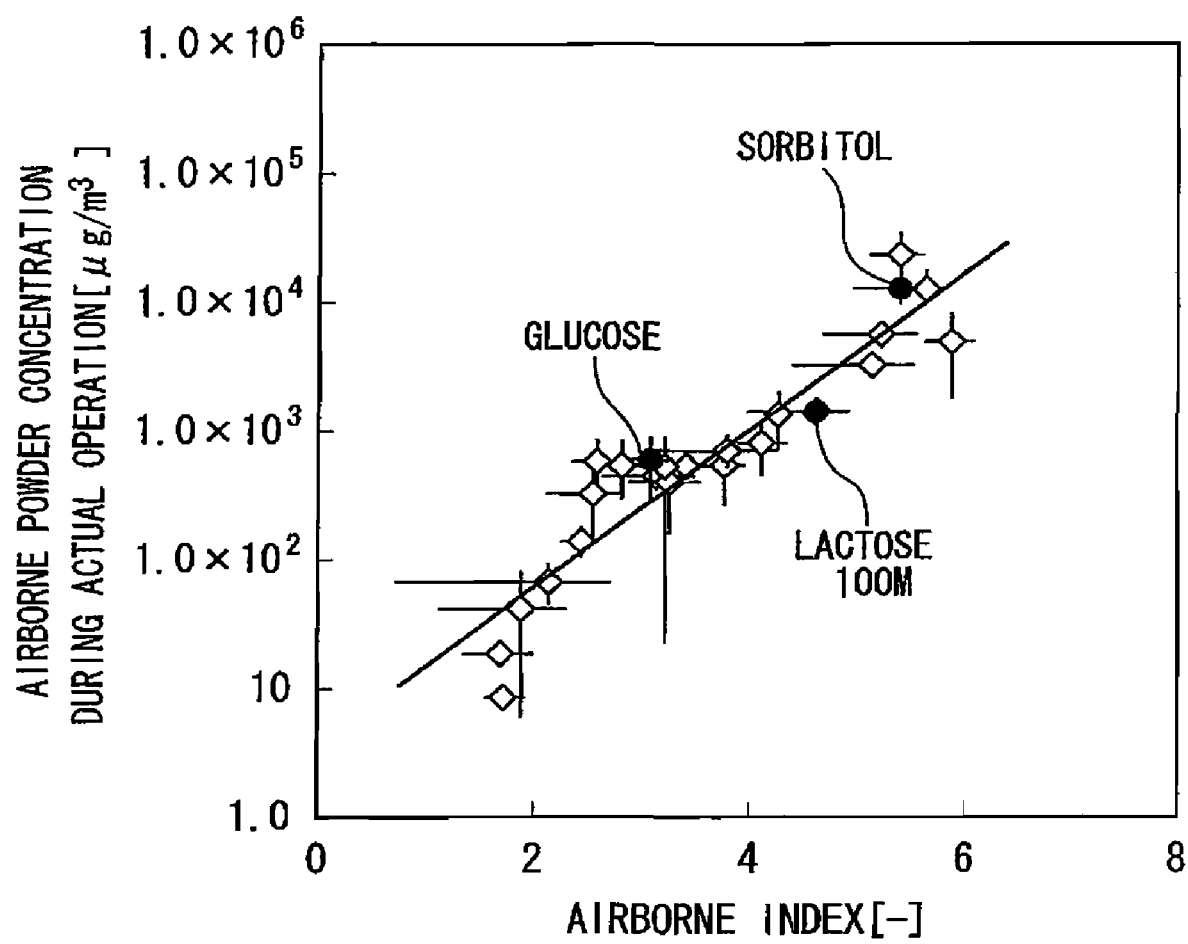
FIG. 7 is a graph showing a relationship between the airborne index, which is obtained by the method for evaluating the powder dispersibility according to the present invention, and the airborne powder concentration in the actual operation in Example 6 of the present invention.

The airborne index obtained in the measurement G was plotted against the airborne powder concentration obtained in the measurement H for the respective powders and an approximation curve was obtained by the linear regression of these plotted points due to the employment of the least squares method. Results are shown in FIG. 7.

From the obtained approximation curve, it was confirmed that the airborne index obtained in the measurement G was almost proportional to the logarithm of the airborne powder concentration obtained in the measurement H.

Therefore, even when the powder mass was only 0.1 g, it was confirmed that the airborne powder concentration of the actual target powder in the actual operation can be predicted.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A method for evaluating powder dispersibility comprising the steps of:
   dispersing a powder allowed to stand inside a closed container by mechanical vibration applied quantitatively to the powder using a vibratory device;
   drawing air inside the closed container that contains the dispersed powder into an apparatus,
   collecting the dispersed powder on a quartz crystal element provided in the apparatus; and
   measuring a mass of the collected powder using a quartz crystal microbalance and the volume of air drawn into the apparatus to thereby measure an airborne powder concentration in air inside the closed container based on the mass of the powder and the volume of air collected in the apparatus.

2. The method for evaluating powder dispersibility according to claim 1, wherein the mass of the powder allowed to stand inside the closed container is within a range from 0.1 g to 5 g.

3. A method for evaluating airborne powder concentration comprising the steps of:
   measuring an airborne powder concentration of a surrogate powder by the method of claim 1 or 2 for evaluating powder dispersibility;
   calculating a logarithm of the airborne powder concentration (airborne index d);
   measuring an airborne concentration C' of the surrogate powder in a working environment;
   producing a calibration curve F(d) from the airborne index d and the airborne concentration C'; and
   predicting an airborne concentration C of an actual target powder in the working environment from the airborne index d of the actual target powder using the calibration curve F(d).

4. A method of designing a powder containment facility comprising the steps of:
   predicting dispersibility of an actual target powder in an actual working environment by the method of claim 3 for evaluating airborne powder in concentration; and
   designing a powder containment facility based on a predicted result.

5. The method for assessing powder dispersibility according to claim 1, wherein the apparatus is a cascade impactor.

6. The method for assessing powder dispersibility according to claim 1, wherein the volume of the closed container is within a range of 100 ml to 300 ml.

7. The method for assessing powder dispersibility according to claim 1, wherein a period for applying mechanical vibration is within a range of 10 to 15 seconds.

* * * * *